US00PP23029P2

(12) United States Plant Patent
Bergman

(10) Patent No.: US PP23,029 P2
(45) Date of Patent: Sep. 11, 2012

(54) *CHRYSANTHEMUM* PLANT NAMED 'CIDZ0005'

(50) Latin Name: *Chrysanthemum×morifolium*
Varietal Denomination: CIDZ0005

(75) Inventor: Wendy R. Bergman, Gilroy, CA (US)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 13/136,011

(22) Filed: Jul. 20, 2011

(51) Int. Cl.
*A01H 5/00* (2006.01)

(52) U.S. Cl. ..... Plt./295

(58) Field of Classification Search ..... Plt./295, Plt./296
See application file for complete search history.

*Primary Examiner* — Kent L Bell
(74) *Attorney, Agent, or Firm* — Joshua L. Price

(57) ABSTRACT

A new *Chrysanthemum* plant named 'CIDZ0005' particularly distinguished by the daisy anemone type, clear yellow ray floret color (but can show a bronze coloring when grown in cold greenhouses) with a green disc, excellent flowering uniformity and high temperature performance, medium yellow-green foliage, and vigorous growth habit.

1 Drawing Sheet

Latin name of the genus and species of the plant claimed: *Chrysanthemum×morifolium.*

Varietal denomination: 'CIDZ0005'.

BACKGROUND OF THE NEW PLANT

The present invention comprises a new *Chrysanthemum*, botanically known as *Chrysanthemum×morifolium*, and hereinafter referred to by the variety name 'CIDZ0005'.

'CIDZ0005' is a product of a planned breeding program. The new cultivar has a daisy anemone type, clear yellow ray floret color (but can show a bronze coloring when grown in cold greenhouses) with a green disc, excellent flowering uniformity and high temperature performance, medium yellow-green foliage, and vigorous growth habit.

'CIDZ0005' originated from a hybridization made in February 2006 in a controlled breeding environment in Salinas, Calif., USA. The female parent was the proprietary plant designated 'YB-A7630', unpatented, with yellow ray floret color, different inflorescence form and less plant vigor.

The male parent of 'CIDZ0005' was an unpatented, proprietary plant identified as 'YB-B0094' with white ray floret color and produces pollen.

'CIDZ0005' was selected as one flowering plant within the progeny of the stated cross in November 2006 in a controlled environment in Fort Myers, Fla. USA.

The first act of asexual reproduction of 'CIDZ0005' was accomplished when vegetative cuttings were propagated from the initial selection in December 2006, in a controlled environment in Fort Meyers, Fla. USA.

BRIEF SUMMARY OF INVENTION

Horticultural examination of plants grown from cuttings of the plant initiated in February 2007, and continuing thereafter, has demonstrated that the combination of characteristics as herein disclosed for 'CIDZ0005' are firmly fixed and are retained through successive generations of asexual reproduction.

'CIDZ0005' has not been observed under all possible environmental conditions. The phenotype may vary significantly with variations in environment such as temperature, light intensity and day length.

A Plant Breeder's Right for this cultivar was applied for in Canada on Aug. 17, 2010 (10-7063). 'CIDZ0005' has not been made publicly available more than -one year prior to the filing of this application.

The following traits have been repeatedly observed and are determined to be basic characteristics of the new variety. The combination of these characteristics distinguishes this *Chrysanthemum* as a new and distinct variety.

BRIEF DESCRIPTION OF THE PHOTOGRAPHS

The accompanying photographic drawing shows typical inflorescence and foliage characteristics of 'CIDZ0005' with colors being as true as possible with an illustration of this type. The photographic drawing shows four flowering potted plants of the new variety and a close-up of the inflorescence.

DETAILED BOTANICAL DESCRIPTION

The plant descriptions, measurements and aforementioned photographs were taken in Gilroy, Calif. in early May 2011 under natural light. These plants were propagated and grown in Nipomo, Calif. and shipped to Gilroy, Calif. for the data collection and photographs. These plants were approximately 11 weeks of age; grown as four plants together in a six inch pot under greenhouse trial conditions.

Color references are made to The Royal Horticultural Society Colour Chart (R.H.S.) 2001.

TABLE 1

DIFFERENCES BETWEEN THE NEW VARIETY 'CIDZ0005' AND A SIMILAR VARIETY

| | 'CIDZ0005' | 'Yellow Yograceland' (U.S. Plant Pat. No. 17,451) |
|---|---|---|
| Inflorescence diameter: | Smaller | Larger |
| Growth habit: | Fuller plant | Less full |
| Foliage length: | Longer | Shorter |
| Quantity of disc florets: | Longer | Shorter |
| Quantity of disc florets: | More | Less |

Plant:

*Form, growth and habit*.—Herbaceous pot-type, stems upright and outwardly spreading, freely branching, more controlled habit.

*Plant height*.—20.0 cm.

*Plant height (inflorescence included)*.—26-27.0 cm.

*Plant width*.—18-23.0 cm.

Roots:

*Number of days to initiate roots*.—About 4 days at about 22 degrees C.

*Number of days to produce a rooted cutting*.—About 10 days at 22 degrees C.

*Type*.—Fine, fibrous, free branching.

*Color*.—RHS N155B but whiter.

Foliage:

*Arrangement*.—Alternate, simple.

*Immature, leaf color, upper surface*.—RHS 147A.

*Lower surface*.—RHS 147B.

*Mature, leaf color, upper surface*.—RHS 147A.

*Lower surface*.—RHS 147B.

*Length*.—6.6-8.0 cm.

*Width*.—5.0-6.5 cm.

*Shape*.—Ovate to broadly ovate.

*Base shape*.—Attenuate.

*Apex shape*.—Acute to mucronulate.

*Margin*.—Somewhat lobed; irregularly serrate.

*Texture, upper surface*.—Bifid T-shaped hairs.

*Lower surface*.—Bifid T-shaped hairs.

*Color of veins, upper surface*.—RHS 138B.

*Color of veins, lower surface*.—RHS 138B.

*Petiole color*.—RHS 138B.

*Length*.—1.5-2.4 cm.

*Diameter*.—0.4-0.5 cm.

*Texture*.—Bifid T-shaped hairs.

Stem:

*Quantity of main branches per plant*.—5-6.

*Color of stem*.—RHS 138A.

*Length of stem*.—20-23.0 cm.

*Diameter*.—0.5 cm.

*Length of internodes*.—1.5-3.0 cm.

*Texture*.—Bifid T-shaped hairs.

*Color of peduncle*.—RHS 138A.

*Length of peduncle*.—10-10.3 cm.

*Peduncle diameter*.—0.2 cm.

*Texture*.—Bifid T-shaped hairs.

Inflorescence:

*Type*.—Compositae type, solitary inflorescence, daisy-type and a later developing anemone type, borne terminally above foliage, ray florets arranged acropetally on a capitulum.

*Quantity of short days to flowering (response time)*.—About 8 weeks.

*Quantity of inflorescences per plant*.—20-30.

*Lastingness of individual blooms on the plant*.—About 4 weeks.

*Fragrance*.—Slightly spicy.

Bud (just when opening/showing color):

*Color*.—RHS 5B to RHS 5C.

*Length*.—1.1-1.4 cm.

*Width*.—1.4 cm.

*Shape*.—Oblate.

Immature inflorescence:

*Diameter*.—About 5.0 cm.

*Color of ray florets, upper surface*.—RHS 5B.

*Lower surface*.—RHS 5C; some with RHS 34C to RHS 34D straitions basally.

Mature inflorescence:

*Diameter*.—7-7.5 cm.

*Depth*.—Variable from 3.3-4.5 cm.

*Total diameter of 'disc'*.—3.0-4.0 cm.

*Receptacle height*.—0.5 cm.

*Receptacle diameter*.—0.7-0.8 cm.

Ray florets:

*Average quantity of florets*.—20-24 in 1-2 whorls.

*Color of florets, upper surface*.—RHS 5B some with slight hints of a light RHS 35C striations basally.

*Lower surface*.—RHS 7C with hints of sprinkles of a light hue of RHS 35C.

*Length*.—3.9-4.6 cm.

*Width*.—1.0-1.1 cm.

*Shape*.—Elliptical with slightly rolled margins.

*Apex shape*.—Broadly mucronulate.

*Margin*.—Entire.

*Texture, upper surface*.—Papillose.

*Lower surface*.—Papillose.

Disc florets:

*Average quantity of florets on both sides*.—Approximately 80 immature and 130 mature.

*Color of florets*.—RHS 3B with between RHS 143A and RHS 144A apex; maturing to RHS 3B with RHS 3A apex; many also have some striations of about RHS 35B to RHS 35C.

*Length*.—1.6-2.3 cm.

*Width*.—0.3-0.5 cm.

*Shape*.—Tubular, elongated.

*Apex shape*.—Acute, 5 pointed.

Phyllaries:

*Quantity*.—20.

*Color, upper surface*.—RHS 137C.

*Lower surface*.—RHS 137B.

*Length*.—0.5-0.8 cm.

*Width*.—0.2-0.3 cm.

*Shape*.—Lanceolate.

*Apex shape*.—Acute.

*Base*.—Fused.

*Margins*.—Entire; papery.

*Texture, upper surface*.—Glabrous.

*Lower surface*.—Bifid T-shaped hairs.

Reproductive organs:

*Pistil*.—1.

*Found on both florets*.—Yes.

*Length*.—0.5-0.6 cm.

*Style color*.—RHS 1B but greener.

*Style length*.—0.5-0.55 cm.

*Stigma color*.—RHS 1A.

*Stigma shape*.—Bi-parted.

*Ovary color*.—Not observed.

*Stamens*.—4.

*Found on only disc florets*.—Yes.
*Color of filaments*.—RHS 1D.
*Length filaments*.—0.2 cm.
*Anther color*.—RHS 14B.
*Anther length*.—0.1 cm.
*Anther shape*.—Oblong.
*Color of pollen*.—N/A.
*Pollen amount*.—None observed.
*Fertility/seed set*.—Has not been observed on this hybrid.

Disease/pest resistance: Disease/pest resistance has not been observed on this hybrid.

What is claimed is:

1. A new and distinct variety of *Chrysanthemum* plant named 'CIDZ0005' substantially as illustrated and described herein.

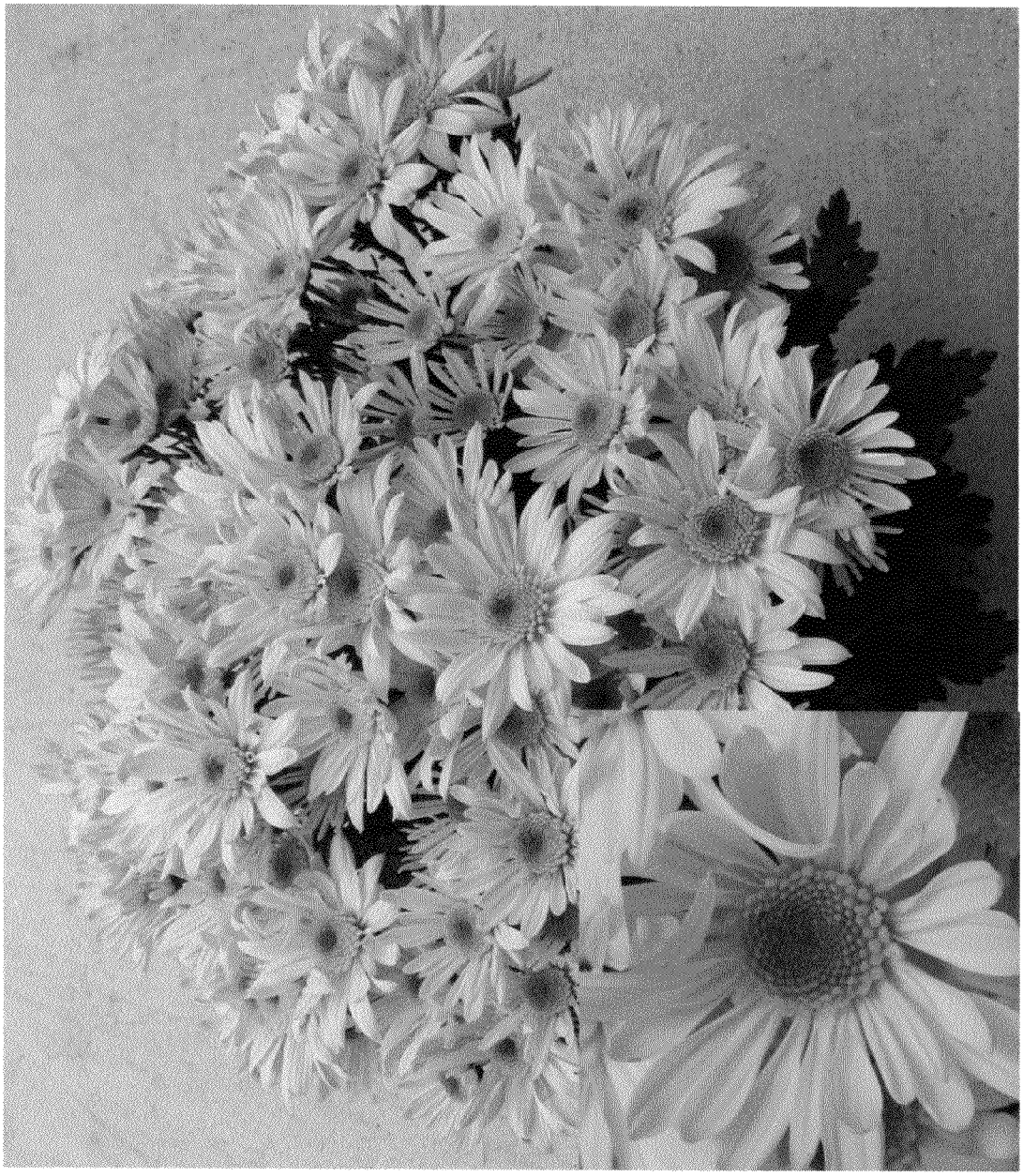

* * * * *